(12) United States Patent
McCormack et al.

(10) Patent No.: US 7,312,167 B2
(45) Date of Patent: Dec. 25, 2007

(54) BREATHABLE MULTILAYER FILMS FOR USE IN ABSORBENT ARTICLES

(75) Inventors: Ann Louise McCormack, Cumming, GA (US); Roger Bradshaw Quincy, III, Cumming, GA (US); Charles Edward Edmundson, Roswell, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 388 days.

(21) Appl. No.: 10/328,758

(22) Filed: Dec. 23, 2002

(65) Prior Publication Data

US 2004/0122388 A1 Jun. 24, 2004

(51) Int. Cl.
*B32B 5/26* (2006.01)
*B32B 27/12* (2006.01)
*B32B 5/02* (2006.01)
*B32B 9/02* (2006.01)

(52) U.S. Cl. .................. 442/381; 442/94; 442/121; 442/382; 442/394; 442/395; 442/400; 442/401; 442/409; 442/417; 428/304.4; 428/306.6; 428/315.5; 428/323; 428/327; 428/317.9

(58) Field of Classification Search ............... 442/394, 442/395, 400, 401, 409, 417, 381, 382, 121; 442/94; 428/304.4, 306.6, 315.5, 323, 327, 428/317.9
See application file for complete search history.

(56) References Cited

U.S. PATENT DOCUMENTS

| 3,338,992 A | 8/1967 | Kinney |
| 3,341,394 A | 9/1967 | Kinney |
| 3,502,538 A | 3/1970 | Petersen |
| 3,502,763 A | 3/1970 | Hartmann |
| 3,542,615 A | 11/1970 | Dobo et al. |
| 3,692,618 A | 9/1972 | Dorschner et al. |
| 3,802,817 A | 4/1974 | Matsuki et al. |
| 3,849,241 A | 11/1974 | Butin et al. |
| 4,340,563 A | 7/1982 | Appel et al. |
| 4,539,982 A | 9/1985 | Bailly |
| 4,789,699 A | 12/1988 | Kieffer et al. |
| 5,008,296 A | 4/1991 | Antoon, Jr. et al. |
| 5,230,958 A | 7/1993 | Dabi |

(Continued)

FOREIGN PATENT DOCUMENTS

DE 19603840 A1 8/1997

(Continued)

OTHER PUBLICATIONS

Product Data Bulletin for Nuchar® RGC 40—Developmental Product, Westvaco Chemicals, 1 page.

(Continued)

*Primary Examiner*—Norca L. Torres-Velazquez
(74) *Attorney, Agent, or Firm*—Dority & Manning, P.A.

(57) ABSTRACT

A multilayer, breathable film that contains a base layer and at least one skin layer is provided. The skin layer is incorporated with a filler that is capable of reducing odor. The base layer may be substantially free of the odor-reducing filler to maintain the integrity of the resulting film. As a result, it has been discovered that the multilayer film of the present invention can be used to reduce odor in a variety of applications, while still maintaining the desired breathability.

21 Claims, 2 Drawing Sheets

U.S. PATENT DOCUMENTS

| | | | |
|---|---|---|---|
| 5,272,236 A | 12/1993 | Lai et al. | |
| 5,322,728 A | 6/1994 | Davey et al. | |
| 5,382,400 A | 1/1995 | Pike et al. | |
| 5,407,442 A * | 4/1995 | Karapasha | 604/359 |
| 5,429,628 A * | 7/1995 | Trinh et al. | 604/359 |
| 5,472,775 A | 12/1995 | Obijeski et al. | |
| 5,571,619 A | 11/1996 | McAlpin et al. | |
| 5,695,868 A | 12/1997 | McCormack | |
| 5,834,114 A | 11/1998 | Economy et al. | |
| 5,843,057 A | 12/1998 | McCormack | |
| 5,855,999 A | 1/1999 | McCormack | |
| 5,883,028 A | 3/1999 | Morman et al. | |
| 5,910,136 A | 6/1999 | Hetzler et al. | |
| 5,955,187 A | 9/1999 | McCormack et al. | |
| 6,002,064 A | 12/1999 | Kobylivker et al. | |
| 6,037,281 A | 3/2000 | Mathis et al. | |
| 6,045,900 A | 4/2000 | Haffner et al. | |
| 6,072,005 A * | 6/2000 | Kobylivker et al. | 525/240 |
| 6,075,179 A | 6/2000 | McCormack et al. | |
| 6,090,325 A | 7/2000 | Wheat et al. | |
| 6,096,299 A | 8/2000 | Guarracino et al. | |
| 6,114,024 A | 9/2000 | Forte | |
| 6,156,421 A | 12/2000 | Stopper et al. | |
| 6,309,736 B1 | 10/2001 | McCormack et al. | |
| 6,348,258 B1 | 2/2002 | Topolkaraev et al. | |
| 6,414,217 B1 | 7/2002 | Uitenbroek et al. | |
| 6,682,803 B2 * | 1/2004 | McCormack et al. | 428/138 |
| 2001/0024716 A1 | 9/2001 | Chen et al. | |
| 2002/0004350 A1 | 1/2002 | Morman et al. | |
| 2002/0110689 A1* | 8/2002 | Hu et al. | 428/375 |
| 2002/0137420 A1* | 9/2002 | Dacey et al. | 442/389 |

FOREIGN PATENT DOCUMENTS

| | | |
|---|---|---|
| EP | 0510619 A1 | 10/1992 |
| EP | 0806195 A1 | 11/1997 |
| EP | 0850617 A1 | 7/1998 |
| EP | 1192886 A1 * | 4/2002 |
| GB | 898104 | 6/1962 |
| WO | WO 9619346 A2 | 6/1996 |
| WO | WO 9619346 A3 | 6/1996 |
| WO | WO 9912734 A1 | 3/1999 |
| WO | WO 0197972 A1 | 12/2001 |

OTHER PUBLICATIONS

PCT Search Report, Dec. 30, 2003.

* cited by examiner

BREATHABLE MULTILAYER FILMS FOR USE IN ABSORBENT ARTICLES

BACKGROUND OF THE INVENTION

Vapor permeable, liquid impermeable (e.g., breathable) polymeric films are generally known in the art. For instance, one method of making a polymeric film vapor permeable involves mixing a matrix polymer with an organic or inorganic particulate filler (e.g., calcium carbonate), and extruding a film from the blend. The film is then heated and stretched, causing voids to form in the areas surrounding the filler particles. The voided film is characterized by thin polymer membranes and/or fine pore networks that permit the molecular diffusion of water vapor through the film, but which block the passage of liquids. In essence, a tortuous path is created from one film surface to the other which permits transfer of vapors but not liquids.

In many absorbent articles (e.g., diapers), these breathable films are employed as a back sheet. Filled, stretched polyolefin films provide good water vapor transmission, making the absorbent article more comfortable to the wearer. As a result, the relative humidity and temperature within the absorbent article can be reduced by using breathable films. However, one common problem associated with such articles is their inability to effectively reduce odors produced by the absorbed fluids.

As such, a need currently exists for an effective mechanism of reducing odor in an absorbent article.

SUMMARY OF THE INVENTION

In accordance with one embodiment of the present invention, a breathable, multilayer film is disclosed that includes a base layer that contains a thermoplastic polymer, the base layer having a first exterior surface and a second exterior surface. A skin layer is positioned adjacent to the first exterior surface of the base layer. The skin layer contains a thermoplastic polymer and an odor-reducing particulate filler. In some embodiments, for instance, the odor-reducing particulate filler is selected from the group consisting of activated carbon, zeolites, silica, alumina, magnesia, titania, clay, cyclodextrin and derivatives thereof, and combinations thereof.

The odor-reducing particulate filler can have a median particle size of less than about 100 microns, in some embodiments from about 10 nanometers to about 100 microns, and in some embodiments, from about 0.5 microns to about 50 microns. The odor-reducing particulate filler(s) (whether one or more fillers are utilized) constitute from about 1% to about 75% by weight of the skin layer, in some embodiments from about 5% to about 50% by weight of the skin layer, and in some embodiments, from about 5% to about 25% by weight of the skin layer. Moreover, the skin layer may have a thickness of from about 1% to about 25% of the total thickness of the multilayer film, and in some embodiments, from about 2% to about 10% of the total thickness of the multilayer film.

If desired, the multilayer film may also contain a second skin layer positioned adjacent to the second exterior surface of the base layer. In some embodiments, the second skin layer contains a thermoplastic polymer and an odor-reducing particulate filler. For example, the odor-reducing particulate filler(s) may constitute from about 1% to about 75% by weight of the second skin layer, and in some embodiments, from about 5% to about 50% by weight of the second skin layer.

The resulting film may have a water vapor transmission rate greater than about 1,000 grams per square meter per 24 hours ($g/m^2/24$ hours), in some embodiments greater than about 5,000 $g/m^2/24$ hours, and in some embodiments, greater than about 10,000 $g/m^2/24$ hours.

In accordance with another embodiment of the present invention, an absorbent article (e.g., diaper, training pant, incontinence device, sanitary napkin, wound covering, etc.) is disclosed that comprises an absorbent core disposed between a liquid permeable top sheet and a back sheet. The back sheet includes a breathable, multilayer film. The multilayer film comprises a base layer that contains a thermoplastic polymer and a particulate filler, the base layer having a first exterior surface and a second exterior surface. A first skin layer is positioned adjacent to the first exterior surface of the base layer. The first skin layer contains a thermoplastic polymer and an odor-reducing particulate filler. The odor-reducing particulate filler(s) (whether one or more are utilized) constitute from about 1% to about 75% by weight of the skin layer. A second skin layer is also positioned adjacent to the first exterior surface of the base layer. The film has a water vapor transmission rate greater than about 1,000 $g/m^2/24$ hours.

Other features and aspects of the present invention are discussed in greater detail below.

BRIEF DESCRIPTION OF THE DRAWINGS

A full and enabling disclosure of the present invention, including the best mode thereof, directed to one of ordinary skill in the art, is set forth in the specification, which makes reference to the appended drawings, in which.

Repeat use of reference characters in the present specification and drawings is intended to represent the same or analogous features or elements of the invention.

DETAILED DESCRIPTION OF REPRESENTATIVE EMBODIMENTS

Definitions

As used herein, an "absorbent article" refers to any article capable of absorbing water or other fluids. Examples of some absorbent articles include, but are not limited to, personal care absorbent articles, such as diapers, training pants, absorbent underpants, fenestration materials, adult incontinence products, feminine hygiene products (e.g., sanitary napkins), swim wear, baby wipes, and so forth; medical absorbent articles, such as garments, underpads, bandages, absorbent drapes, and medical wipes; food service wipers; clothing articles; and so forth. Materials and processes suitable for forming such absorbent articles are well known to those skilled in the art.

As used herein, the term "breathable" means previous to water vapor and gases, but impermeable to liquid water. For instance, "breathable barriers" and "breathable films" allow water vapor to pass therethrough, but are substantially impervious to liquid water. The "breathability" of a material is measured in terms of water vapor transmission rate (WVTR), with higher values representing a more breathable material and lower values representing a less breathable material.

As used herein the term "nonwoven fabric" or "nonwoven web" means a web having a structure of individual fibers or threads which are interlaid, but not in an identifiable manner as in a knitted fabric. Some examples of nonwoven fabrics or webs include, but are not limited to, meltblown webs, spunbonded webs, airlaid webs, bonded carded webs, etc.

As used herein, the term "meltblown web" refers to a nonwoven web formed by extruding a molten thermoplastic material through a plurality of fine, usually circular, die capillaries as molten fibers into converging high velocity gas (e.g. air) streams that attenuate the fibers of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Butin, et al., which is incorporated herein in its entirety by reference thereto for all purposes. Generally speaking, meltblown fibers may be microfibers that may be continuous or discontinuous, are generally smaller than 10 microns in diameter, and are generally tacky when deposited onto a collecting surface.

As used herein, the term "spunbonded web" refers to a nonwoven web containing small diameter substantially continuous fibers that are formed by extruding a molten thermoplastic material as filaments from a plurality of fine, usually circular, capillaries of a spinnerette with the diameter of the extruded fibers then being rapidly reduced as by, for example, eductive drawing and/or other well-known spunbonding mechanisms. The production of spunbonded nonwoven webs is described and illustrated, for example, in U.S. Pat. No. 4,340,563 to Appel, et al., U.S. Pat. No. 3,692,618 to Dorschner, et al., U.S. Pat. No. 3,802,817 to Matsuki, et al., U.S. Pat. No. 3,338,992 to Kinney, U.S. Pat. No. 3,341,394 to Kinney, U.S. Pat. No. 3,502,763 to Hartman, U.S. Pat. No. 3,502,538 to Levy, U.S. Pat. No. 3,542,615 to Dobo, et al., and U.S. Pat. No. 5,382,400 to Pike, et al., which are incorporated herein in their entirety by reference thereto for all purposes. Spunbond fibers are generally not tacky when they are deposited onto a collecting surface. Spunbond fibers may sometimes have diameters less than about 40 microns, and are often between about 5 to about 20 microns.

DETAILED DESCRIPTION

Reference now will be made in detail to various embodiments of the invention, one or more examples of which are set forth below. Each example is provided by way of explanation, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention cover such modifications and variations.

In general, the present invention is directed to a multilayer, breathable film that contains a base layer and at least one skin layer. The skin layer includes a filler that is capable of reducing odor. As a result, it has been discovered that the multilayer film of the present invention can be used to reduce odor in a variety of applications, while still maintaining the desired breathability.

Figure 1:
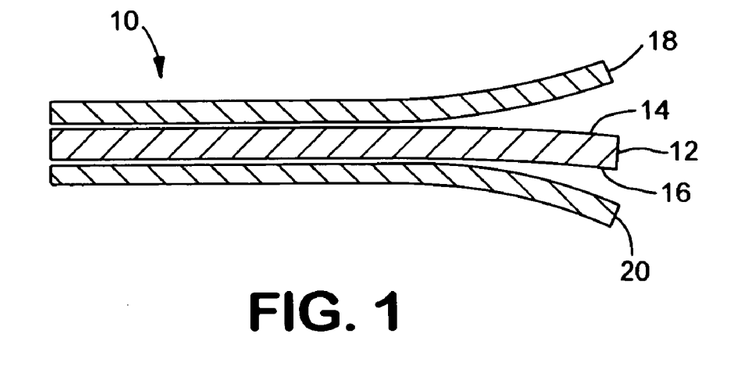
FIG. 1 is a cross-sectional side view of a multilayer film formed according to one embodiment of the present invention in which the right side of the film has been split apart for exemplary purposes.

Referring to FIG. 1, for instance, one embodiment of a multilayer film 10 is shown that, for purposes of illustration, has been split apart at the right side of the drawing. The multilayer film 10 includes a base layer 12 made from an extrudable thermoplastic polymer, such as a polyolefin or a blend of polyolefins. The base layer 12 has a first exterior surface 14 and a second exterior surface 16. Attached to the first exterior surface 14 of the base layer 12 is a first skin layer 18 and attached to the second exterior surface 16 of the base layer 12 is a second skin layer 20. Although the multilayer film 10 is shown as having three layers, it should be understood that the film 10 may have any number of layers desired, so long as it contains a base layer and at least one skin layer.

The base layer 12, the first skin layer 18, and the second skin layer 20 may be formed from any polymers that are capable of being utilized in multilayer film constructions including, but not limited to, homopolymers, copolymers, blends thereof, and so forth. In one particular embodiment, a polyolefin polymer may be used that is a predominately linear polyolefin polymer, such as linear, low-density polyethylene (LLDPE) or polypropylene. The term "linear low density polyethylene" refers to polymers of ethylene and higher alpha olefin comonomers, such as $C_3$-$C_{12}$ and combinations thereof, having a Melt Index (as measured by ASTM D-1238) of from about 0.5 to about 30 grams per 10 minutes at 190° C. Moreover, the term "predominately linear" means that the main polymer chain is linear with less than about 5 long chain branches per 1000 ethylene units. Long chain branches include, for example, carbon chains greater than $C_{12}$. For predominately linear polyolefin polymers that are nonelastic, short chain branching ($C_3$-$C_{12}$) due to comonomer inclusion is typically less than about 20 short chains per 1000 ethylene units and about 20 or greater for polymers that are elastomeric. Examples of predominately linear polyolefin polymers include, without limitation, polymers produced from the following monomers: ethylene, propylene, 1-butene, 4-methyl-pentene, 1-hexene, 1-octene and higher olefins as well as copolymers and terpolymers of the foregoing. In addition, copolymers of ethylene and other olefins including butene, 4-methyl-pentene, hexene, heptene, octene, decene, etc., are also examples of predominately linear polyolefin polymers. Additional film-forming polymers that may be suitable for use with the present invention, alone or in combination with other polymers, include ethylene vinyl acetate (EVA), ethylene ethyl acrylate (EEA), ethylene acrylic acid (EAA), ethylene methyl acrylate (EMA), ethylene normal butyl acrylate (EnBA), polyester (PET), nylon, ethylene vinyl alcohol (EVOH), polystyrene (PS), polyurethane (PU), polybutylene (PB), and polybutylene terephthalate (PBT).

The polymer(s) used to form the film 10 may be prepared using a Ziegler-Natta catalyst system, a metallocene catalyst system, and so forth. Metallocene-catalyzed polyolefins are described, for instance, in U.S. Pat. No. 5,571,619 to McAlpin et al.; U.S. Pat. No. 5,322,728 to Davis et al.; U.S. Pat. No. 5,472,775 to Obijeski et al.; U.S. Pat. No. 5,272,236 to Lai et al.; and U.S. Pat. No. 6,090,325 to Wheat, et al., which are incorporated herein in their entirety by reference thereto for all purposes. Examples of metallocene catalysts include bis(n-butylcyclopentadienyl)titanium dichloride, bis (n-butylcyclopentadienyl)zirconium dichloride, bis(cyclopentadienyl)scandium chloride, bis(indenyl)zirconium dichloride, bis(methylcyclopentadienyl)titanium dichloride, bis(methylcyclopentadienyl)zirconium dichloride, cobaltocene, cyclopentadienyltitanium trichloride, ferrocene, hafnocene dichloride, isopropyl(cyclopentadienyl,-1-flourenyl)zirconium dichloride, molybdocene dichloride, nickelocene, niobocene dichloride, ruthenocene, titanocene dichloride, zirconocene chloride hydride, zirconocene dichloride, and so forth. Polymers made using metallocene catalysts typically have a narrow molecular weight range. For instance, metallocene-catalyzed polymers can have polydispersity numbers (Mw/Mn) of below 4, controlled short chain branching distribution, and controlled isotacticity.

For the base layer 12, the polymer matrix typically constitutes from about 30% to about 80% by weight of the layer, in some embodiments from 40% to about 65% by weight of the layer, and in some embodiments, from about 45% to about 60% by weight of the layer. Likewise, for the skin layers 18 and/or 20, the polymer matrix typically constitutes from about 25% to about 99% by weight of the layer, in some embodiments from 50% to about 97% by weight of the layer, and in some embodiments, from about 75% to about 95% by weight of the layer.

Regardless of the particular polymer(s) used to form the multilayer film 10, one or more of the skin layers 18 and 20 contain a filler that functions to reduce odor. Any filler that is capable of reducing odor by adsorbing a certain odiferous agent (e.g., dimethyl disulfide (DMDS), triethylamine (TEA), ammonia, etc.) may be used in the present invention. The effectiveness of most fillers in reducing odor may be measured in terms of the "Relative Adsorption Efficiency" in accordance with Headspace Gas Chromatography set forth herein. For instance, the "Relatively Adsorption Efficiency" of DMDS for most films formed according to the present invention is at least about 2 milligrams of DMDS adsorbed per gram of the film (mg/g), and in some embodiments, at least about 10 mg/g. In addition, the "Relatively Adsorption Efficiency" of TEA for most films formed according to the present invention is at least about 2 milligrams of TEA adsorbed per gram of the film (mg/g), and in some embodiments, at least about 4 mg/g. It should be recognized that the pore structure and surface chemistry of any one kind of odor-reducing filler or film may not be suitable to reduce all types of odors, and that low adsorption of one or more odiferous agents may be compensated by good adsorption of other odorants.

Some examples of odor-reducing fillers that may be used in the present invention include, but are not limited to, activated carbon, zeolites, silica, alumina, magnesia, titania, clay, cyclodextrin and derivatives thereof, combinations thereof, and so forth. For instance, suitable forms of activated carbon and techniques for formation thereof are described in U.S. Pat. No. 5,834,114 to Economy, et al.; WO 01/97972 to Economy, et al.; and U.S. Patent Publication No. 2001/0024716, which are incorporated herein in their entirety by reference thereto for all purposes. Some commercially available examples of activated carbon are made from saw dust, wood, charcoal, peat, lignite, bituminous coal, coconut shells, and so forth. One particular example of activated carbon that may be used in the present invention is Nuchar® RGC 40, a granular activated carbon available from Westvaco Chemicals. RGC 40 can be provided with a U.S. Mesh Size of 40×100 (150 to 425 microns), and ground to any desired median particle size, such as about 1 micron.

Further, odor-adsorbing forms of zeolites are also well known in the art. For instance, zeolites generally have an aluminate/silicate framework, with associated cations, M, providing overall electrical neutrality. Empirically, the zeolite framework can be represented as follows:

with the electrically neutral zeolite represented as follows:

wherein, x and y are each integers, M is a cation, and n is the charge on the cation. As noted by the empirical formula, zeolites may also contain water ($zH_2O$). M can be a wide variety of cations, e.g., $Na^+$, $K^+$, $NH_4^+$, alkylammonium, heavy metals, and so forth. Still other forms of suitable zeolites may be described in U.S. Pat. No. 6,096,299 to Guarracino, et al., which is incorporated herein in its entirety by reference thereto for all purposes. Moreover, some examples of cyclodextrins that may be suitable for use in the present invention include, but are not limited to, α-cyclodextrin, hydroxyalkyl α-cyclodextrin, alkyl α-cyclodextrin, β-cyclodextrin, hydroxyalkyl β-cyclodextrin, alkyl β-cyclodextrin, y-cyclodextrin, hydroxyalkyl γ-cyclodextrin, and alkyl γ-cyclodextrin.

It should be understood that the odor-reducing filler may be present in only one skin layer of the film, or may be present in two or more skin layers. In addition, any given skin layer may contain one or more odor-reducing fillers, either alone, or in conjunction with one or more conventional fillers, such as calcium carbonate. Moreover, the odor-reducing filler may also be coated with a fatty acid, such as stearic acid or behenic acid, and/or other materials to facilitate the free flow of the particles (in bulk) and their ease of dispersion into the polymer.

The particle size and concentration of filler within the skin layers 18 and/or 20 can be varied as desired depending on a variety of factors, such as the nature of the filler particle, the nature of the film polymer, the desired level of odor reduction, etc. For instance, larger filler levels and particles sizes may result in the formation of voids in the film upon stretching that may have an adverse affect on the integrity of the film. On the other hand, smaller filler levels and particle sizes may result in insufficient odor reduction. Thus, in most embodiments of the present invention, the filler level within a given skin layer is from about 1% to about 75% of the total weight the skin layer, in some embodiments from about 5% to about 50% of the total weight of the skin layer, and in some embodiments, from about 5% to about 25% of the total weight of the skin layer. Likewise, the median particle size of the filler is also typically less than about 100 microns, in some embodiments from about 10 nanometers to about 100 microns, and in some embodiments, from about 0.5 microns to about 50 microns. When referred to herein, the "median" particle size refers to the "D50" size of the filler. Specifically, as is well known in the art, the designation "D50" means that at least 50% of the particles have the size indicated. For example, in one embodiment, the odor-reducing filler particles have a D50 size of less than about 10 microns, which means that at least 50% of the particles have a particle size less than 10 microns. Likewise, the same odor-reducing filler particles may also have a D90 size of less than about 25 microns, which means that at least 90% of the particles have a particle size less than 25 microns. It should be understood that certain odor-reducing fillers, such as activated carbon, may be ground or milled to achieve the desired particle size.

Generally speaking, most odor-reducing particulate fillers used in the present invention contain a relatively high level of organic volatiles. The mechanical and thermal stresses placed on the filler during extrusion can sometimes drive off the volatiles from the filler. Without intending to be limited by theory, it is believed that, when driven off, the volatiles cause the polymer matrix to break away from the filler, thereby making a greater surface area of the filler available for adsorbing odiferous agents. In contrast to previous attempts of incorporating such materials within the base layer of a film, the use of an odor-reducing filler in the skin layers 18 and/or 20 does not typically result in degradation of the film's integrity. Specifically, even after the volatiles are driven from the skin layers 18 and/or 20 during extrusion, the film 10 does not lose its integrity because the base layer 12 holds the film 10 together.

The base layer 12 may also contain a filler, which may be the same or different than the filler used in the skin layers 18 and/or 20. As indicated above, it may be desired that the base layer 12 be substantially free of the filler used in the skin layers 18 and/or 20 (e.g., less than about 5% by weight of the layer) so that the film 10 will not lose its integrity when the organic volatiles are driven off during extrusion. In such instances, however, the base layer 12 may nevertheless contain a conventional inorganic or organic filler that is not necessarily tailored to provide a desired level of odor reduction. Examples of such fillers can include, but are not limited to, ($CaCO_3$), various clays, alumina, barium sulfate, talc, magnesium sulfate, titanium dioxide, aluminum sulfate, cellulose-type powders, diatomaceous earth, gypsum, magnesium sulfate, magnesium carbonate, barium carbonate, kaolin, mica, carbon, magnesium oxide, aluminum hydroxide, pulp powder, wood powder, cellulose derivatives, polymeric particles, chitin and chitin derivatives. The filler particles may optionally be coated with a fatty acid, such as stearic acid or behenic acid, and/or other material in order to facilitate the free flow of the particles (in bulk) and their ease of dispersion into the polymer. In reference to the base layer 12, the filled film will usually contain at least about 35% filler based upon the total weight of the layer, and in some embodiments, from about 45% to about 65% of the filler by weight of the layer.

In addition to a filler and polymeric material, other conventional additives, such as melt stabilizers, processing stabilizers, heat stabilizers, light stabilizers, antioxidants, heat aging stabilizers, whitening agents, antiblocking agents, bonding agents, and so forth, may also be incorporated into the layers 12, 18, and/or 20 to impart desired characteristics to the film. Generally, phosphite stabilizers (e.g., IRGAFOS available from Ciba Specialty Chemicals of Terrytown, N.Y. and DOVERPHOS available from Dover Chemical Corp. of Dover, Ohio) are exemplary melt stabilizers. In addition, hindered amine stabilizers (e.g., CHIMASSORB available from Ciba Specialty Chemicals of Terrytown, N.Y.) are exemplary heat and light stabilizers. Further, hindered phenols are commonly used as an antioxidant in the production of films. Some suitable hindered phenols include those available from Ciba Specialty Chemicals of Terrytown, N.Y. under the trade name "Irganox", such as Irganox 1076. Moreover, bonding agents may also be added to the film to facilitate bonding of the multilayer film to additional materials (e.g., nonwoven web). Examples of such bonding agents include hydrogenated hydrocarbon resins. Other suitable bonding agents are described in U.S. Pat. No. 4,789,699 to Kieffer et al. and U.S. Pat. No. 5,695,868 to McCormack, which are incorporated herein in their entirety by reference thereto for all purposes.

The properties of the resulting film 10 may generally vary as desired. For instance, prior to stretching, the film 10 typically has a basis weight of less than about 100 grams per square meter, and in some embodiments, from about 50 to about 75 grams per square meter. Upon stretching, the multilayer film 10 typically has a basis weight of less than about 60 grams per square meter, and in some embodiments, from about 15 to about 35 grams per square meter. The film 10 can also have a total thickness of from about 15 microns to about 50 microns, and in some embodiments, from about 15 to about 30 microns. Generally speaking, the base layer 12 may comprise from about 50% to about 98% of the thickness of the film 10. In addition, each skin layer 18 and 20 may separately comprise from about 1% to about 25% of the total thickness of the film 10, and in some embodiments from about 2% to about 10% of the total thickness of the film 10. Thus, for instance, each skin layer 18 and 20 may separately comprise 3% of the total thickness of the film 10, and together, comprise 6% of the total thickness of the film 10. Further, as indicated above, the film 10 is also generally constructed to function as a breathable microporous film. For instance, the film 10 typically has a water vapor transmission rate of greater than about 1,000 $g/m^2/24$ hours, in some embodiments greater than about 5,000 $g/m^2/24$ hours, and in some embodiments, greater than about 10,000 $g/m^2/24$ hours.

Figure 2:
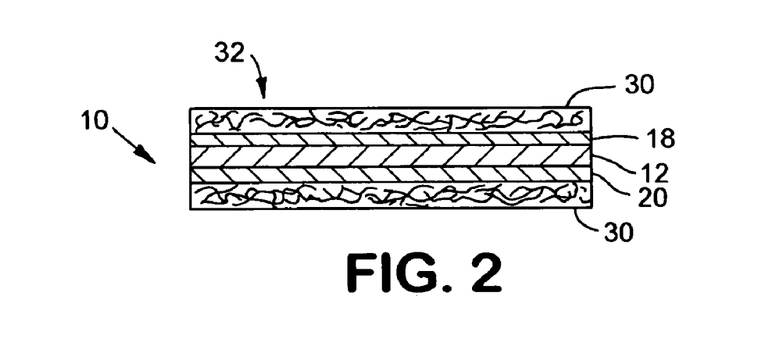
FIG. 2 is a cross-sectional view of a multilayer film/nonwoven laminate formed according to another embodiment of the present invention.

If desired, the resultant multilayer film 10 may be laminated to one or more support layers 30, such as shown in FIG. 2. The support layers 30 shown in FIG. 2 are fibrous nonwoven webs. The fibrous nonwoven web layers 30 can add additional properties to the multilayer film 10, such as, a more soft, cloth-like feel. This is particularly advantageous when the multilayer film 10 is used as a barrier layer to liquids in an outer cover for personal care absorbent articles or as a barrier material for hospital, surgical, and clean room applications. Attachment of the support layers 30 to the first skin layer 18 and second skin layer 20 may be by the use of a separate adhesive, such as hot-melt or solvent based adhesive, or through the use of heat and/or pressure. For instance, suitable techniques for bonding a film to a nonwoven web are described in U.S. Pat. No. 5,843,057 to McCormack; U.S. Pat. No. 5,855,999 to McCormack; U.S. Pat. No. 6,002,064 to Kobylivker, et al.; U.S. Pat. No. 6,037,281 to Mathis, et al.; and WO 99/12734, which are incorporated herein in their entirety by reference thereto for all purposes.

The multilayer film 10 may be formed by a wide variety of processes well known to those of ordinary skill in the art. Two particularly advantageous processes are cast film coextrusion processes and blown film coextrusion processes. In such processes, two or more of the film layers are formed simultaneously and exit the extruder in a multilayer form. Some examples of such processes are described in U.S. Pat. No. 6,075,179 to McCormack, et al. and U.S. Pat. No. 6,309,736 to McCormack, et al., which are incorporated herein in their entirety by reference thereto for all purposes.

Figure 3:
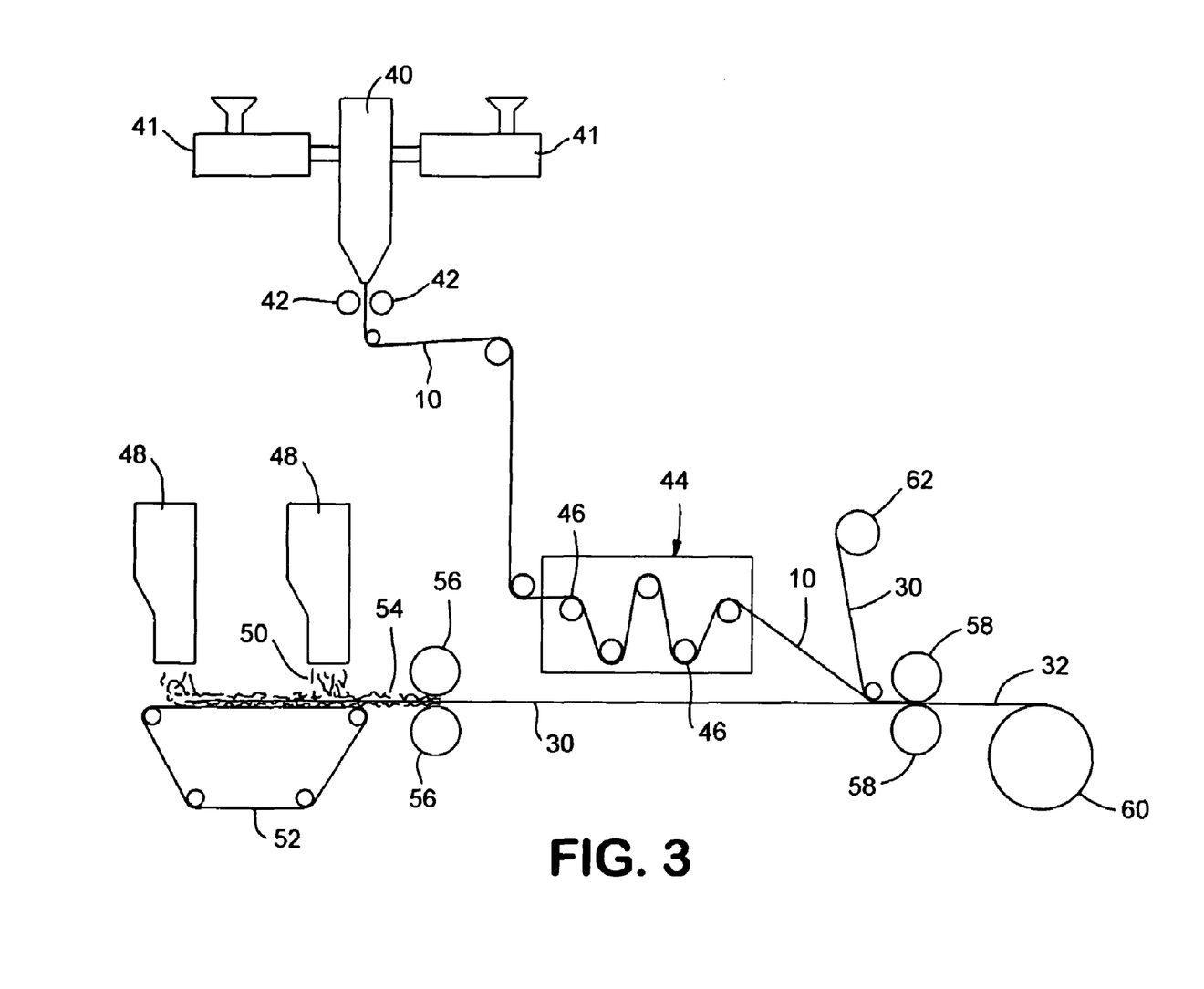
FIG. 3 is a schematic illustration of one embodiment of a process that can be used to form a multilayer film and a multilayer film/nonwoven laminate in accordance with the present invention.

One particular process for forming the multilayer film 10 is shown in FIG. 3. As shown, in this embodiment, the multilayer film 10 is formed using a coextrusion film apparatus 40, such as a cast or blown unit. The apparatus 40 typically includes two or more polymer extruders 41. The multilayer film 10 is extruded into a pair of nip or chill rollers 42, one of which may be patterned so as to impart an embossed pattern to the newly formed film 10. This is particularly advantageous to reduce the gloss of the film and give it a matte finish.

The film 10 is directed from the coextrusion film apparatus 40 to a film-stretching unit 44, such as a machine direction orienter that is a commercially available device from vendors such as the Marshall and Williams Company of Providence, R.I. The apparatus 44 has a plurality of stretching rollers 46 that progressively stretch and thin the multilayer film 10 in the machine direction of the film, i.e., in the direction of travel of the film 10 through the process. The film may be uniaxially stretched, for example, to about 1.1 to about 7.0 times its original length. In some embodiments, the film may be stretched to about 1.5 to about 6.0 times its original length. Further, in some embodiments, the film may be stretched to about 2.5 to about 5.0 times its original length. The film may alternatively be biaxially stretched using techniques familiar to one of ordinary skill in the art, including, but not limited to, sequential, simultaneous, and incremental biaxial stretching techniques.

If desired, the film 10 may be attached to one or more support layers 30 to form a multilayer film/nonwoven laminate 32. Referring again to FIG. 3, a conventional fibrous nonwoven web forming apparatus 48, such as a pair of spunbond machines, is used to form the support layer 30. The long, essentially continuous fibers 50 are deposited onto a forming wire 52 as an unbonded web 54, and the unbonded web 54 is then sent through a pair of bonding rolls 56 to bond the fibers together and increase the tear strength of the resultant web support layer 30. One or both of the rolls are sometimes heated to aid in bonding. Typically, one of the rolls 56 is also patterned so as to impart a discrete bond pattern with a prescribed bond surface area to the web 30. The other roll is usually a smooth anvil roll, but this roll also may be patterned if so desired. Once the film 10 has been sufficiently thinned and oriented and the support layer 30 has been formed, the two layers are brought together and laminated to one another using a pair laminating rolls or other means 58. As with the bonding rolls 56, the laminating rolls 58 may be heated. Also, at least one of the rolls may be patterned to create a discrete bond pattern with a prescribed bond surface area for the resultant laminate 32. Although not required, the maximum bond point surface area for a given area of surface on one side of the laminate 32 typically does not exceed about 50% of the total surface area. Once the laminate 32 exits the laminating rolls 58, it may be wound up into a roll 60 for subsequent processing. Alternatively, the laminate 32 may continue in-line for further processing or conversion.

The process shown in FIG. 3 may also be used to create a three layer laminate 32, such as is shown in FIG. 2. For instance, the above-described process may be modified with a supply 62 of a second fibrous nonwoven web support layer 30 into the laminating rolls 58 on a side opposite that of the other fibrous nonwoven web support layer 30. As shown in FIG. 3, the supply of support layer 30 is in the form of a preformed roll 62. Alternatively, as with the other layers, the support layer 30 may be formed directly in-line. In either event, the second support layer 30 may be fed into the laminating rolls 58 and laminated to the film 10 in the same fashion as the other support layer 30.

Figure 4:
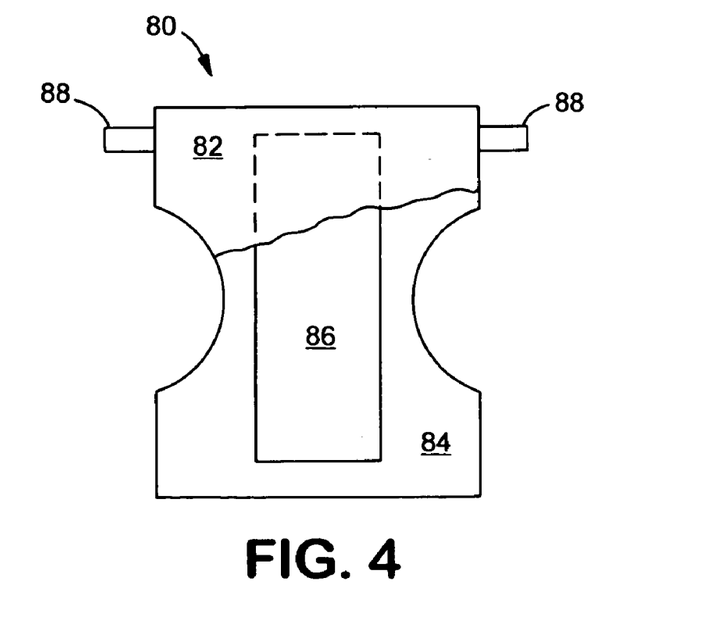
FIG. 4 is a partially cut away top plan view of one embodiment of a personal care article that may be formed according to the present invention.

As stated above, the multilayer film 10 and/or the laminate 32 may be used in a wide variety of applications, such as in personal care absorbent articles (e.g., diapers, training pants, incontinence devices) and feminine hygiene products (e.g., sanitary napkins). Referring to FIG. 4, an exemplary diaper 80 is illustrated that includes a liquid permeable top sheet or liner 82, a liquid-impermeable back sheet or outercover 84, and an absorbent core 86 disposed between and contained by the top sheet 82 and back sheet 84. The diaper 80 may also include a fastening device 88, such as adhesive fastening tapes or mechanical hook and loop type fasteners. In one embodiment, the multilayer film 10 and/or the multilayer film/support layer laminate 32 may be used to form the top sheet 82.

As a result of the present invention, it has been discovered that a breathable, multilayer film may be formed that has the ability to reduce odors by incorporating an odor-reducing filler into one or more skin layers of the film. Moreover, by being contained within the skin layer(s), the integrity of the film can be substantially maintained, even after the organic volatiles of the filler are driven off during extrusion.

The present invention may be better understood with reference to the following examples.

EXAMPLE 1

The ability to form a multi-layer film of the present invention was demonstrated. The film contained a base layer surrounded by two skin layers. The base layer contained 58% by weight of the layer of OMYAFILM® 2 SS T-FL, which is a calcium carbonate filler obtained from Omya, Inc. of Proctor, Vt. that has a 2 micron median particle size. The calcium carbonate filler was coated with 0.85% stearic acid. The base layer also included 19% by weight of the layer of Dowlex 2517 linear low polyethylene and 23% by weight of the layer Dowlex 2047A linear low polyethylene, which are available from Dow Plastics, a division of Dow Chemical Company of Midland, Mich.

Each skin layer contained 40.8% by weight of the layer Basell KS357P catalloy polymer from Basell Polyolefins of Basell North America Inc., Wilmington, Del. The Basell catalloy is an olefinic thermoplastic multistep reactor product wherein an amorphous ethylene propylene random copolymer is molecularly dispersed in a predominately semicrystalline high propylene monomer/low ethylene monomer continuous matrix. Each skin layer also contained 25% by weight of the layer ethylene vinyl acetate LD755 and 25% ethylene vinyl acetate LD761. LD755 and LD761 are both available from ExxonMobil Chemical Company of Houston, Tex.

In addition to the above-referenced polymers, the skin layers also contained 5% by weight of the layer Nuchar® RGC 40 activated carbon and 4.2% by weight of the layer low molecularweight polyethylene A-C16 from Honeywell International Inc. of Morristown, N.J. The Nuchar® activated carbon was obtained from MeadWestvaco Corp. of Stamford, Conn., and was subsequently jetmilled by WEDCO of Houston, Tex. to a median particle size of 1 micron. The jetmilled activated carbon was first dispersed in the ethylene vinyl acetate resin, and then compounded into the semicrystalline high propylene monomer/low ethylene monomer continuous matrix.

The three layer film was extruded using cast flat or chill roll extrusion onto a smooth chill roll. The die temperature was 204° C., the cast roll temperature was 26.7° C. The air gap between the film die tip and the chill roll was approximately 7 millimeters. The film was formed at a speed of 125 feet per minute and stretched 4×(500%) through a machine direction orienter (MDO) in a single zone at 77° C. and annealed at 99° C. By saying the film was stretched 4×, it is meant that, for example, a 1-meter long film would be stretched to a resultant length of 4 meters.

The final basis weight was 18 grams per square meter (gsm).

EXAMPLE 2

A film was also formed as set forth in Example 1 without the odor-reducing filler. In particular, the base layer was identical to that described in Example 1. Each skin layer contained 50% by weight of the layer Basell KS357P catalloy polymer; 25% by weight of the layer ethylene vinyl acetate LD755; and 25% ethylene vinyl acetate LD761.

The final basis weight was 18 grams per square meter (gsm).

RESULTS OF EXAMPLES 1-2

The films of Examples 1 and 2 were tested to compare their breathability and odor reduction capability. Sample A, the film of Example 2, had a combined skin layer thickness that was 3% of the overall thickness of the film. Three samples (B-D) of the film described in Example 1 were also evaluated. The samples B-D were identical to each other, except that the skin layer thickness for the samples B-D was 3%, 5% and 8% of the total film thickness, respectively.

Breathability

Breathability was measured for Samples A-D in terms of the "water vapor transmission rate" (WVTR), which generally refers to the rate at which water vapor permeates through a material as measured in units of grams per meter squared per 24 hours ($g/m^2/24$ hrs). The WVTR was determined using the test procedure standardized by INDA (Association of the Nonwoven Fabrics Industry), number IST-70.4-99, entitled "STANDARD TEST METHOD FOR WATER VAPOR TRANSMISSION RATE THROUGH NONWOVEN AND PLASTIC FILM USING A GUARD FILM AND VAPOR PRESSURE SENSOR." The INDA test method is well known and is described in U.S. Pat. No. 6,414,217 to Uitenbroek, et al., which is incorporated herein in its entirety by reference thereto for all purposes.

The test procedure is generally summarized as follows. A dry chamber was initially separated from a wet chamber of known temperature and humidity by a permanent guard film and the sample material to be tested. The purpose of the guard film was to define a definite air gap and to quiet or still the air in the air gap while the air gap is characterized. The dry chamber, guard film, and the wet chamber formed a diffusion cell in which the test film was sealed. The sample holder was the Permatran-W model 100K, manufactured by Modern Controls, Inc. of Minneapolis, Minn.

A first test was made of the WVTR of the guard film and air gap between an evaporator assembly that generated 100% relative humidity. Water vapor diffused through the air gap and the guard film, and then mixed with a dry gas flow that was proportional to water vapor concentration. The electrical signal was routed to a computer for processing. The computer calculated the transmission rate of the air gap and guard film and stores the value for further use. The transmission rate of the guard film and air gap was stored in the computer as CalC. The sample material was then sealed in the test cell. Again, water vapor diffused through the air gap to the guard film and the test material, and then mixed with a dry gas flow that swept the test material. Also, again, this mixture was carried to the vapor sensor. The computer then calculated the transmission rate of the combination of the air gap, the guard film, and the test material. This information was used to calculate the transmission rate at which moisture is transmitted through the test material according to the equation:

$$TR^{-1}_{test\ material} = TR^{-1}_{testmaterial,\ guardfilm,\ airgap} - TR^{-1}_{guardfilm,\ airgap}$$

WVTR was calculated as follows:

$$WVTR = F\rho_{sat}(T)RH/AP_{sat}(T)(1-RH))$$

wherein,

F=The flow of water vapor in cubic centimeters per minute;

$\rho_{sat}(T)$=The density of water in saturated air at temperature T;

RH=The relative humidity at specified locations in the cell;

A=The cross-sectional area of the cell; and $P_{sat}$=The saturation vapor pressure of water vapor at temperature T.

Using the test set forth above, it was determined that the WVTR of Samples A-D was 17,080; 21,680; 22,700; and 13,020 $g/m^{21}/24$ hours, respectively. Thus, the breathability of Samples B and C was clearly maintained after incorporation with activated carbon.

Odor Reduction

The ability of Samples A-D to adsorb certain odiferous compounds was determined using a test known as "Headspace Gas Chromatography." Dimethyl disulfide (DMDS, Aldrich, 99.0+%) was used to determine the ability of Samples A-D to remove malodorous sulfur compounds. Triethylamine (TEA, Aldrich, 99.5%) was used to determine the ability of Samples A-D to remove malodorous amine compounds.

The headspace gas chromatography testing was conducted on an Agilent Technologies 5890, Series II gas chromatograph with an Agilent Technology 7694 headspace sampler (Agilent Technologies, Waldbronn, Germany). Helium was used as the carrier gas (injection port pressure: 12.7 psig; headspace vial pressure: 15.8 psig; supply line pressure is at 60 psig). A DB-624 column was used for the triethylamine (TEA) and dimethyl disulfide (DMDS) that had a length of 30 meters and an internal diameter of 0.25 millimeters. Such a column is available from J&W Scientific, Inc. of Folsom, Calif.

The operating parameters used for the headspace gas chromatography are shown below in Table 1:

TABLE 1

Operating Parameters for the Headspace Gas Chromatography Device.
Headspace Parameters

| | | |
|---|---|---|
| Zone Temps, ° C. | Oven | 37 |
| | Loop | 42 |
| | TR. Line | 47 |
| Event Time, minutes | GC Cycle time | 10.0 |
| | Vial eq. Time | 10.0 |
| | Pressuriz. Time | 0.20 |
| | Loop fill time | 0.20 |
| | Loop eq. Time | 0.15 |
| | Inject time | 0.30 |
| Vial Parameters | First vial | 1 |
| | Last vial | 1 |
| | Shake | [off] |

The test procedure involved placing 0.12 grams of the film sample in a 20-cubic centimeter headspace vial. Using a syringe, an aliquot of the odoriferous agent (TEA or DMDS) was also placed in the vial. The vial was then sealed with a cap and a septum and placed in the headspace gas chromatography oven at 37° C. After ten minutes, a hollow needle was inserted through the septum and into the vial. A 1-cubic centimeter sample of the headspace (air inside the vial) was then injected into the gas chromatograph.

Initially a control vial with only the aliquot of odoriferous agent (TEA or DMDS) was tested to define 0% odoriferous agent adsorption. To calculate the amount of headspace odoriferous agent removed by the film, the peak area for the odoriferous agent from the vial with the film was compared to the peak area from the odoriferous agent control vial. Testing was done with 3.8 milligrams of DMDS (3.6 microliters), 2.2 milligrams of TEA (3.0 microliters), and ca. 0.12 grams of the sample. Each sample was tested in duplicate.

The results are set forth below in Tables 2-3 in terms of milligrams (mg) odor adsorbed per gram (g) of the film sample, i.e., the "Relative Adsorption Efficiency." The results represent the average of two samples for each type of film.

TABLE 2

Removal of TEA

| Sample | Weight (g) | Relative Adsorption Efficiency (mg odor removed/g sample) | % Odor removed |
| --- | --- | --- | --- |
| A | 0.1191 | 3.57 | 19.57 |
| B | 0.1180 | 3.70 | 20.15 |
| C | 0.1193 | 3.39 | 18.63 |
| D | 0.1196 | 4.00 | 22.08 |

TABLE 3

Removal of DMDS

| Sample | Weight (g) | Relative Adsorption Efficiency (mg odor removed/g sample) | % Odor removed |
| --- | --- | --- | --- |
| A | 0.1237 | 9.09 | 29.85 |
| B | 0.1166 | 10.81 | 33.46 |
| C | 0.1223 | 11.23 | 36.44 |
| D | 0.1219 | 12.81 | 41.46 |

As indicated, Samples B-D generally had a higher adsorption of DMDS and TEA than Sample A.

EXAMPLE 3

The ability to form a multi-layer film of the present invention was demonstrated. The film contained a base layer surrounded by two skin layers. The base layer contained 58% by weight of the layer of OMYAFILM® 2 SS T-FL, which is a calcium carbonate filler obtained from Omya, Inc. of Proctor, Vt. that has a 2 micron median particle size. The calcium carbonate filler was coated with 0.85% stearic acid. The base layer also included 19% by weight of the layer of Dowlex 2517 linear low polyethylene and 23% by weight of the layer Dowlex 2047A linear low polyethylene, which are available from Dow Plastics, a division of Dow Chemical Company of Midland, Mich.

Each skin layer contained 35.8% by weight of the layer Basell KS357P catalloy polymer from Basell Polyolefins of Basell North America Inc., Wilmington, Del. The Basell catalloy is an olefinic thermoplastic multistep reactor product wherein an amorphous ethylene propylene random copolymer is molecularly dispersed in a predominately semicrystalline high propylene monomer/low ethylene monomer continuous matrix. Each skin layer also contained 25% by weight of the layer ethylene vinyl acetate LD755 and 25% ethylene vinyl acetate LD761. LD755 and LD761 are both available from ExxonMobil Chemical Company of Houston, Tex.

In addition to the above-referenced polymers, the skin layers also contained 10% by weight of the layer Nuchar® RGC 40 activated carbon and 4.2% by weight of the layer low molecular weight polyethylene A-C16 from Honeywell International Inc. of Morristown, N.J. The Nuchar® activated carbon was obtained from MeadWestvaco of Stamford, Conn., and was subsequently jetmilled by WEDCO of Houston, Tex. to a median particle size of 1 micron. The jetmilled activated carbon was first dispersed in the ethylene vinyl acetate resin, and then compounded into the semicrystalline high propylene monomer/low ethylene monomer continuous matrix.

The three-layer film was extruded using cast flat or chill roll extrusion onto a smooth chill roll. The die temperature was 204° C., the cast roll temperature was 26.7° C. The air gap between the film die tip and the chill roll was approximately 7 millimeters. The film was formed at a speed of 125 feet per minute and stretched 4×(500%) through a machine direction orienter (MDO) in a single zone at 77° C. and annealed at 99° C. By saying the film was stretched 4×, it is meant that, for example, a 1-meter long film would be stretched to a resultant length of 4 meters.

The final basis weight was 18 grams per square meter (gsm).

RESULTS OF EXAMPLE 3

Various samples were tested to compare their odor reduction capability as described above. Sample E, the film of Example 2, had a combined skin layer thickness that was 3% of the overall thickness of the film. Two samples (F & G) of the film described in Example 3 were also evaluated. The samples F & G were identical to each other, except that the skin layer thickness for the Samples F & G was 3% and 5% of the total film thickness, respectively.

The results are set forth below in Tables 4-5 in terms of milligrams (mg) odor adsorbed per gram (g) of the film sample, i.e., the "Relative Adsorption Efficiency." The results represent the average of two samples for each type of film.

TABLE 4

Removal of TEA

| Sample | Weight (g) | Relative Adsorption Efficiency (mg odor removed/g sample) | % Odor removed |
| --- | --- | --- | --- |
| E | 0.1191 | 3.57 | 19.57 |
| F | 0.1202 | 3.09 | 17.13 |
| G | 0.1163 | 2.81 | 15.10 |

TABLE 5

| | Removal of DMDS | | |
| --- | --- | --- | --- |
| Sample | Weight (g) | Relative Adsorption Efficiency (mg odor removed/g sample) | % Odor removed |
| E | 0.1237 | 9.09 | 29.85 |
| F | 0.1180 | 10.45 | 32.71 |
| G | 0.1223 | 10.86 | 35.25 |

As indicated, Samples F & G generally had a higher adsorption of DMDS than Sample E. Although Samples F & G exhibited a lower adsorption of TEA than Sample E, it should be understood that the pore structure and surface chemistry of any given odor-reducing filler or film may not be suitable to reduce all types of odors, and that low adsorption of one or more malodorous compounds may be compensated by good adsorption of other malodorous compounds.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. An absorbent article comprising an absorbent core disposed between a liquid permeable layer and a liquid-impermeable layer, wherein the liquid-impermeable layer contains a film comprising:
    a base layer that contains a thermoplastic polymer and a filler, the base layer having a first exterior surface and a second exterior surface, wherein the base layer contains less than about 5% by weight of activated carbon particles; and
    a first skin layer positioned adjacent to the first exterior surface of the base layer, the first skin layer containing a thermoplastic polymer and activated carbon particles that constitute from about 1% to about 75% by weight of the skin layer;
    wherein the film has a water vapor transmission rate greater than about 1,000 grams per square meter per 24 hours.

2. The absorbent article of claim 1, wherein the activated carbon particles constitute from about 5% to about 25% by weight of the skin layer.

3. The absorbent article of claim 1, wherein the activated carbon particles have a median particle size of less than about 100 microns.

4. The absorbent article of claim 1, wherein the activated carbon particles have a median particle size of from about 0.5 microns to about 50 microns.

5. The absorbent article of claim 1, wherein the activated carbon particles have a median particle size of less than about 10 microns.

6. The absorbent article of claim 1, wherein the filler of the base layer includes calcium carbonate.

7. The absorbent article of claim 1, wherein the first skin layer has a thickness of from about 1% to about 25% of the total thickness of the film.

8. The absorbent article of claim 1, wherein the first skin layer has a thickness of from about 2% to about 10% of the total thickness of the film.

9. The absorbent article of claim 1, further comprising a second skin layer positioned adjacent to the second exterior surface of the base layer.

10. The absorbent article of claim 9, wherein the second skin layer contains a thermoplastic polymer and an odor-reducing filler.

11. The absorbent article of claim 10, wherein the odor-reducing filler constitutes from about 5% to about 50% by weight of the second skin layer.

12. The absorbent article of claim 1, wherein the film has a water vapor transmission rate greater than about 5,000 grams per square meter per 24 hours.

13. The absorbent article of claim 1, wherein the film has a water vapor transmission rate greater than about 10,000 grams per square meter per 24 hours.

14. The absorbent article of claim 1, wherein the liquid-impermeable layer further includes a first nonwoven web positioned adjacent to the film.

15. The absorbent article of claim 14, wherein the liquid-impermeable layer further includes a second nonwoven web positioned adjacent to the film so that the film is sandwiched between the first and the second nonwoven fibrous webs.

16. The absorbent article of claim 1, wherein the absorbent article is selected from the group consisting of diapers, training pants, incontinence devices, sanitary napkins, and wound coverings.

17. The absorbent article of claim 1, wherein the Relative Adsorption Efficiency of the film for dimethyl disulphide is at least about 2 milligrams of dimethyl disulphide per gram of the film.

18. The absorbent article of claim 1, wherein the Relative Adsorption Efficiency of the film for dimethyl disulphide is at least about 5 milligrams of dimethyl disulphide per gram of the film.

19. The absorbent article of claim 1, wherein the Relative Adsorption Efficiency of the film for triethylamine is at least about 2 milligrams of triethylamine per gram of the film.

20. The absorbent article of claim 1, wherein the Relative Adsorption Efficiency of the film for triethylamine is at least about 4 milligrams of triethylamine per gram of the film.

21. The absorbent article of claim 1, wherein the activated carbon particles constitute from about 5% to about 50% by weight of the skin layer.

* * * * *